Figure 1:
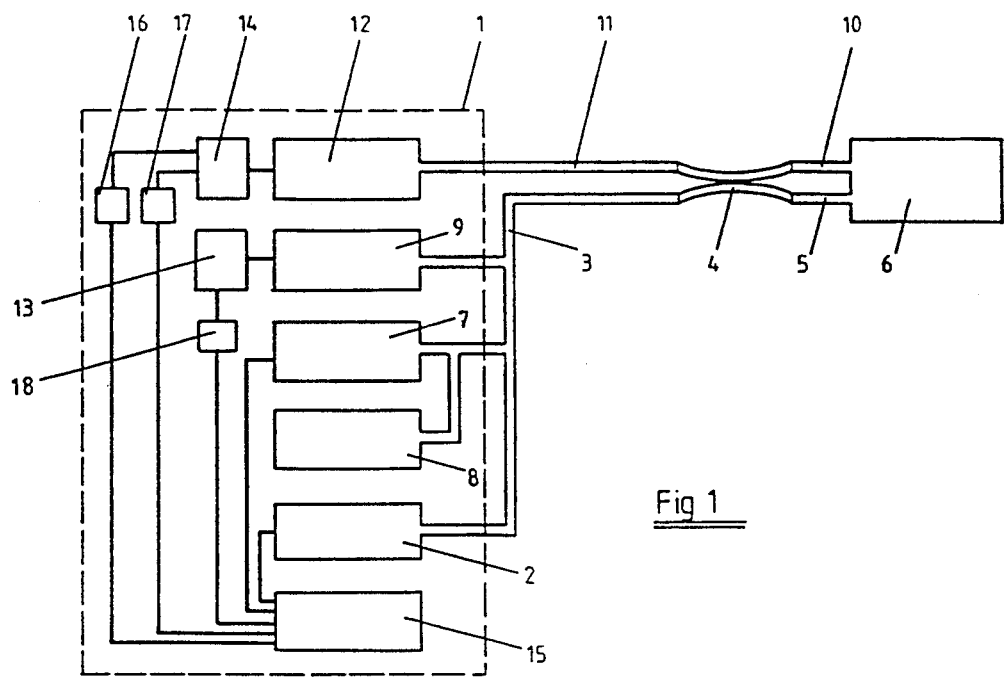

United States Patent [19]

Rantala et al.

[11] Patent Number: 5,301,676
[45] Date of Patent: Apr. 12, 1994

[54] IDENTIFICATION METHOD FOR A CUFF TYPE IN A NON-INVASIVE SPHYGMOMANOMETER

[75] Inventors: Börje T. Rantala, Helsinki; Lauri Kankkunen, Espoo, both of Finland

[73] Assignee: Instrumentarium Corporation, Finland

[21] Appl. No.: 807,111

[22] Filed: Dec. 13, 1991

[30] Foreign Application Priority Data

Dec. 18, 1990 [FI] Finland .................................. 906255

[51] Int. Cl.$^5$ ............................................... A61B 5/02
[52] U.S. Cl. ................................... 128/686; 128/672; 128/677
[58] Field of Search .............. 128/685, 686, 672, 677, 128/679–683

[56] References Cited

U.S. PATENT DOCUMENTS

| | | | |
|---|---|---|---|
| 4,471,646 | 9/1984 | Walker | 128/685 |
| 4,501,280 | 2/1985 | Hood . | |
| 5,003,981 | 4/1991 | Kankkunen . | |
| 5,022,403 | 6/1991 | LaViola | 128/685 |
| 5,038,790 | 8/1991 | Malkamäki | 128/685 |
| 5,060,654 | 10/1991 | Malkamäki . | |

*Primary Examiner*—Randall L. Green
*Assistant Examiner*—Rob Clarke
*Attorney, Agent, or Firm*—Andrus, Sceales, Starke & Sawall

[57] ABSTRACT

The invention relates to an automatic identification method for the cuff of a sphygmomanometer. When changing the pressure in a cuff (6 or 19) or in a space in flow communication therewith, the pressure change occurring in this space is monitored at two spaced-apart measuring points by means of one or a plurality of pressure-sensing means (12 and/or 9) and the pressure signals obtained from these two measuring points are compared to each other and, on the basis of the conducted comparison, the different cuff types are distinguished from each other as the measured pressure difference indicates a cuff type presently in use.

18 Claims, 2 Drawing Sheets

IDENTIFICATION METHOD FOR A CUFF TYPE IN A NON-INVASIVE SPHYGMOMANOMETER

The present invention relates to an identification method for a cuff type in a non-invasive automatic sphygmomanometer, wherein a flow developed in a cuff or a space in flow communication therewith by the application of a positive pressure is restricted in a manner characteristic of a given cuff type.

In some devices, the selection of cuffs intended for adults and infants is effected by means of a selector switch included in the device. Thus, the selector switch is operated to manually select the mode of operation for the device depending on whether the patient is an adult or an infant. However, this involves a hazard of overlooking to shift the position of a selector switch, e.g. when replacing an adult cuff with one intended for infants. Such oversight could result in a serious injury to infants.

For the automatic identification of a cuff size there is a prior developed method, disclosed in U.S. Pat. No. 4,501,280. A certain pressure is pumped in a cuff and then the cuff pressure is lowered by opening a valve. Opening of the valve produces a sound pulse which travels along a tube to the cuff and further to a sensor which calculates the time lapsed from the valve opening to the arrival of a sound pulse in the sensor. The sound-pulse traveling time to the sensor varies according to a cuff size. This sound-pulse delay time can be further changed by shortening a tube leading to a cuff for newborn babies as compared to the length of a tube leading to a cuff for adults. The sound-pulse delay time can be cut down even further by providing the tube running from valve to cuff with a subsidiary tube, connected directly to the tube leading from cuff to sensor. On the basis of the sound-pulse delay time, a microprocessor detects whether the cuff is an adult or an infant cuff.

One problem in a sound-pulse based solution disclosed in the cited U.S. Patent is the impossibility using tubes of arbitrary length leading from a pressure transmission system to a cuff, since the program of this system is based on measuring the pulse transit time which, on the other hand, is set with certain limits of acceptance. However, certain practical cases require tubes that should be either substantially shorter or longer in length than those used in connection of the system of this cited invention. Tubes of equal length cannot be safely used in connection with cuffs intended for adults and children, since this may complicate the identification of a cuff size.

Another problem is that, if a cuff of different size is required, the entire long tube must be replaced at the same time. The use of a short adapter is not possible.

A tubing, which connects the tube leading from pressure transmission system to cuff and the tube leading from cuff to sensor and which reduces the time used by a sound pulse from valve to sensor, carries the disturbances resulting from pumping and valve opening directly to the sensor. This results in a poorer accuracy of measurement particularly in the case that the system involves a continuous regulation of the cuff pressure.

In another prior known method, a cuff is pumped to a certain pressure, followed by measuring the time spent for dropping the pressure. The basis of this idea is that the outflow of air is dependent on the size of a cuff. The longer the time taken up by outflow, the larger the cuff being used. A problem in this solution is the blocking of a cuff or a cuff tube, which in the worst case can result in the incorrect identification of a cuff size. The blocking or jamming of a tube may increase considerably the time required for the deflation of a cuff.

Efforts have been made to resolve this last-mentioned problem by providing the tube leading from pump and valve to cuff with a tubing, one end of which is in turn connected with the tube extending from cuff to a pressure sensor and by-passes the cuff. On the other hand, this connecting tube causes problems during the course of measurements by carrying the disturbances resulting from pumping and valve opening and closing to the pressure sensor. The accuracy of measurement suffers particularly in the case that regulation of the cuff pressure in the system is carried out on a continuous basis.

The automatic identification of a cuff size can also be effected by measuring a time lapse for pumping some given pressure in a cuff. Thus, the pumping time associated with a larger cuff is longer than in the case of a smaller cuff. Problems in this type of solution include faults in the mains and fluctuations in the characteristics of a pump, possibly leading to serious errors in the identification of a cuff.

The cuff size of a sphygmomanometer can also be identified as disclosed in U.S. Pat. No. 5,003,981. The identification is effected e.g. by monitoring the development of pressure occurring in a cuff upon the completion of pumping with the pressure unable to escape to ambient air. According to the cited patent, the flow is restricted within the system in a manner typical of any given cuff size. Usually a cuff intended e.g. for newborn babies is distinguished from a cuff intended for adults by fitting just one cuff, i.e. usually the one intended for newborn babies, with a separate flow-restriction means whereby the internal pressure development of these two different systems immediately upon the completion of pumping can be made sufficiently different from each other. Thus, downstream of a flow-restricting means, pressure continues to rise despite the completion of pumping until there is an equal pressure on either side of said flow-restricting means. On the other hand, if there is no flow-restricting means, the pressure within the system no longer changes upon the completion of pumping.

In accordance with a cuff-type identification method disclosed in another U.S. Pat. No. 4,060,654, a positive or excess pressure is utilized to trigger a pulse to a pressure sensing means followed by measuring the width of a detected pulse. Generally, a larger cuff is distinguished from a smaller one by utilizing the difference between the factors having an effect on pulse response. In practice, a larger and a smaller cuff are distinguished from each other by using a pulse-response altering means in connection with the identification of one of the cuffs. Thus, the pulse width indicates which cuff size is presently in use.

The identification methods set forth in these two latter applications are as such highly favourable and reliable but, however, the identification process itself is relatively tedious and, thus, the blood pressure measuring results may be delayed.

An object of this invention is to eliminate the above problems. Thus, the object is to provide an automatic cuff identification method, which is independent of fluctuations in the pump characteristics and faults in the mains and is capable of using tubes of arbitrary length which need not be necessarily replaced when substituting for a different size cuff. Another object is to provide a pressure measuring system for intensifying the detectable pressure pulses applied to a cuff. An object is also to provide a relatively quick cuff-type identification method.

The characterizing features of a cuff-type identification method of the invention are set forth in the annexed claims.

The invention relating to the identification of a cuff type is based on monitoring a pressure change occurring in a cuff or a space in flow communication therewith at at least two spaced-apart locations. Thus, a cuff type presently in use is identified by comparing to each other the pressure readings obtained at various measuring points. Thus, the pressure readings measured at various measuring points, preferably simultaneously, either remain unchanged or differ from each other depending on a cuff type being used. For example, the identification of two different cuff types can be based on whether the pressure readings are similar or sufficiently different from each other. The cuff types to be identified are often either a cuff for infants or a cuff for adults.

In order to reliably distinguish the cuff types from each other, the flow in a cuff or in a space in flow communication therewith should be restricted in a different manner when using different cuff types. In practice, this is preferably effected by fitting a flow duct, which is in flow communication with a cuff, with a separate flow-restricting means. When the number of cuff types to be identified is two, it is preferred that just one cuff type be provided with a flow-restricting means.

The measurement of pressure effected during the course of identifying a cuff type must be carried out on either side of a flow-restricting means, at least whenever such means is present. The identification is preferably effected while pumping pressure in a cuff. True enough, the identification is also possible during the deflation of pressure in a cuff but, in any case, a certain amount of pressure must be first pumped in a cuff before the deflation thereof. It is also preferred, even if not necessary, that the identification be effected in connection with each measurement.

Figure 2:
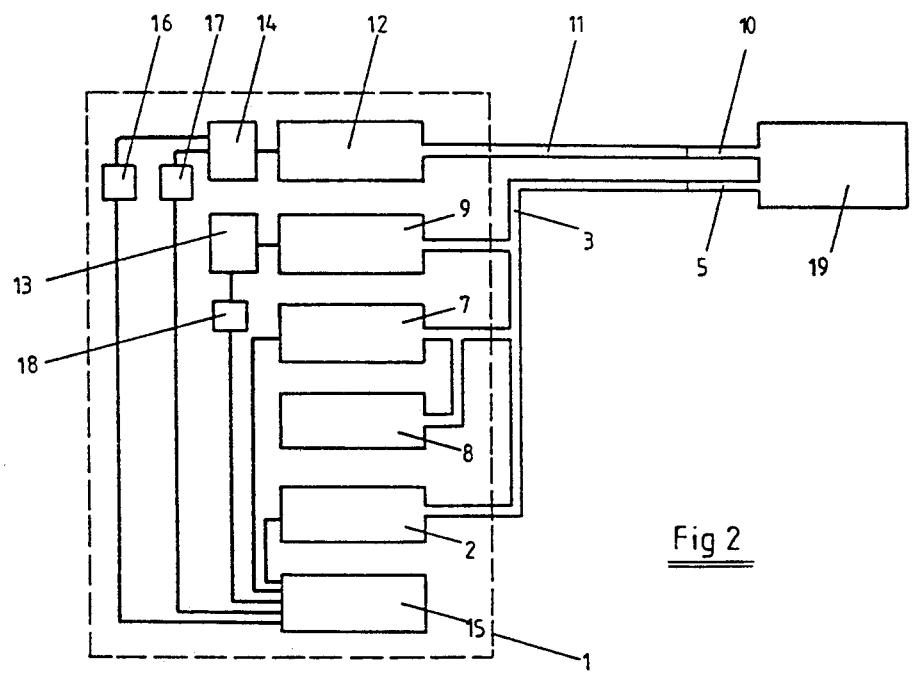
Figure 3:
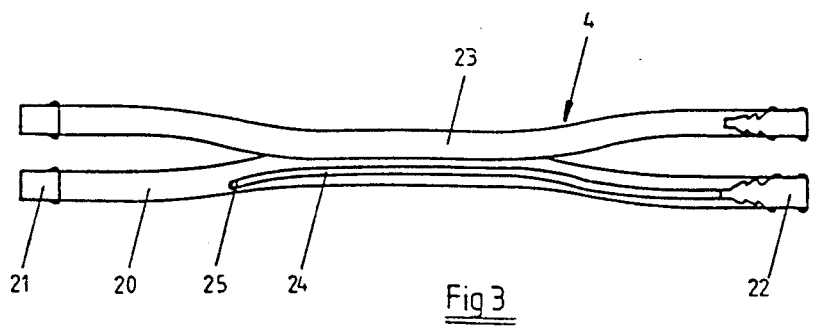
Figure 4A:
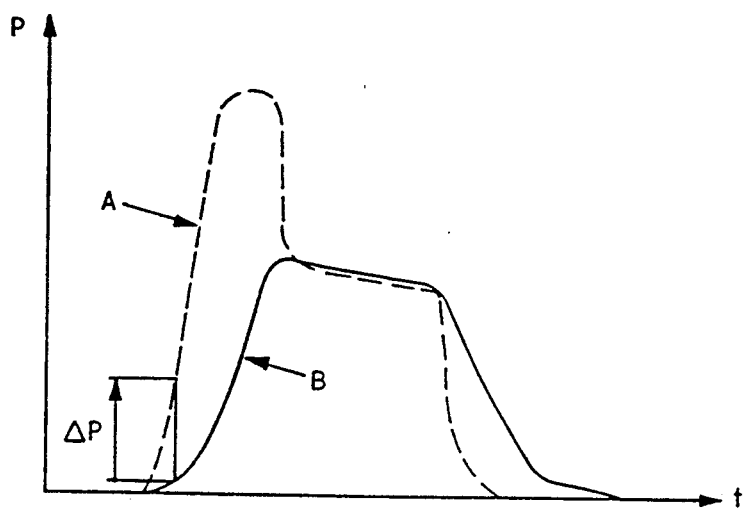
Figure 4B:
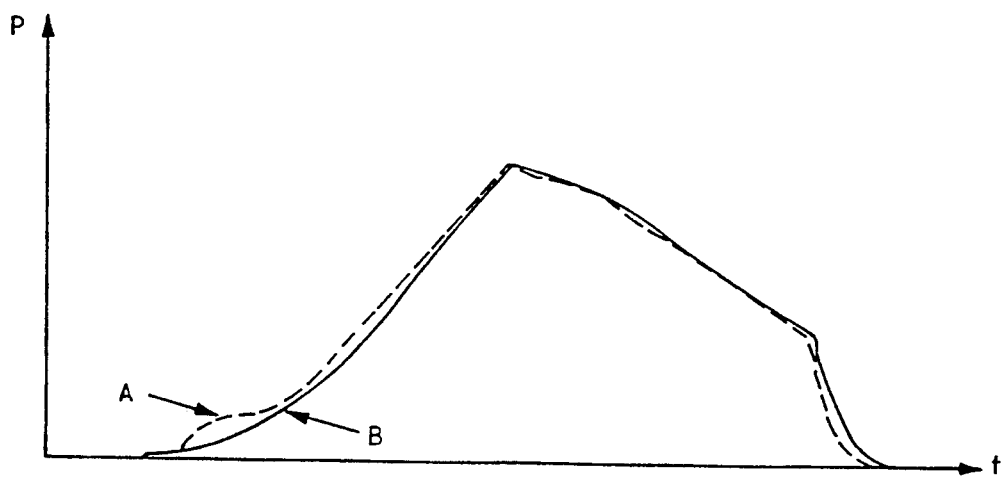

The invention will now be described in more detail with reference made to the accompanying drawings, in which FIG. 1 is a schematic view of an apparatus used in a cuff-type identification method of the invention and provided with a cuff intended for newborn babies, FIG. 2 is a schematic view of an apparatus used in a cuff-type identification method of the invention and provided with a cuff intended for adults, FIG. 3 is a bisected view of one preferred and separate spacer element for use in the cuff-type identification of FIG. 1 and attachable to a tube leading to a cuff, FIGS. 4a and 4b illustrate the principle for an identification method of the invention for distinguishing two different types of cuffs from each other.

FIG. 1 illustrates a schematic view of an apparatus for use in a cuff-type identification method. In the case shown in this figure, the blood pressure is measured on a newborn baby. A monitor 1 is indicated by a dash-and-dot line circumscribing a pump 2, from which a tube 3 extends to a spacer element 4 with a tube 5 extending therefrom further to a cuff 6. In communication with the tube between pump and spacer element is preferably also an outlet valve 7 for discharging some of the air pumped in the cuff, and a pressure-restricting means 8 for releasing a hazardous excess pressure out of the cuff. Furthermore, in communication with tube 3 is preferably a pressure-sensing means 9 for monitoring the pressure prevailing in tube 3. From cuff 6 extends a tube 10 to spacer element 4 and from there another tube 11 to a second pressure-sensing means 12.

The signals received from each pressure-sensing means 9 and 12 travel through AC/DC-signal separators 13 and 14 to a control element 15, the latter also controlling the operation of pump 2 and outlet valve 7. Prior to its arrival in control element 15, the signal coming from signal separator 14 travels through filters 16 and 17 but, instead, signal separator 13 is only used to pass a DC signal to the control element by way of a filter 18. The control element operates on the basis of information received from pressure-sensing means 9 or preferably 12. On the other hand, the identification of a cuff type requires pressure readings picked up at two different locations. This is most preferably effected by means of two separate pressure-sensing means 9 and 12. The control element is preferably a microprocessor.

FIG. 2 illustrates a schematic view of an apparatus for use in a cuff-type identification method relating to the measurement of blood pressure on adults. The only difference from FIG. 1 is that there is no spacer element 4 and an adult cuff 19 is connected directly to tubes 3 and 11 through the intermediary of cuff tubes 5 and 10.

The spacer element 4 is illustrated in more detail in a longitudinal section in FIG. 3. Thus, a tube 20 included in spacer element 4 is attached to a conventional tube 3 extending from pump 2 to cuff 6 by means of a clamping element 21 or 22. The vacant clamping element 22 or 21 is used to attach a cuff 6 to the other end of spacer element tube 20 through the intermediary of tube 5. The spacer element 4 also includes a tube 23 fitted between tubes 10 and 11 extending from cuff 6 to second pressure-sensing means 12. Inside the spacer element tube 20 is a means 24, restricting the flow of a fluid or preferably a gas and provided with an opening 25 for discharging a gas or a fluid. This means is preferably tubular in construction. The diameter of this flow-restricting means can be the larger the longer said means 24 is and of course vice versa. Thus, the means 24 must restrict the flow of gas or fluid to a sufficient degree to make the control element 15 capable of clearly distinguishing a larger and a smaller cuff from each other on the basis of the measurement readings received from pressure-sensing means 9 and 12.

Prior to the identification of a cuff, the pumping is commenced with pump 2 for increasing the pressure in tubes 3 and 11 and in cuff 6 or 19 in flow communication with these tubes. The pressure change occurring during the course of pumping is monitored at two different points, i.e. preferably on either side of a cuff according to the solutions shown in FIGS. 1 and 2. The identification of pressure at two different points is also most preferably effected by means of two separate pressure-sensing means 9 and 12. A pressure signal detected by both pressure-sensing means is carried to control element 15, which effects the relative comparison of pressure readings received from each of said means during the course of pumping.

If the pressure signals detected by the pressure-sensing means are distinctly different from each other, this indicates that there is no unobstructed flow path between the points that the pressure-sensing means receive their signals from. Thus, the control element 15 observes that the flow has been restricted in tubes 3, 5, 10 and 11 extending from pressure-sensing means 9 to cuff 6 or from this cuff to the second pressure-sensing means or therebetween. In the case of FIG. 1, a flow-restricting element 24 is included in a separate spacer element 4 to be clamped between tubes 3 and 5, i.e. it is located between these two pressure-sensing means 9 and 12. The presence of a flow-restricting element indicates further that a smaller cuff, or in this case, a cuff for infants is coupled to spacer element 4.

On the other hand, if the pressure signals detected by the pressure-sensing means remain roughly identical during the course of pumping, said control element 15 identifies the cuff as an adult cuff. In this case, the flow is capable of freely running between the points at which said pressure-sensing means 9 and 12 are sensing the pressure. Thus, no attempts have been made to restrict the flow in tubes 3, 5, 10 and 11 extending from pressure-sensing means 9 to cuff 19 and from there on to second pressure-sensing means 12.

FIGS. 4a and 4b illustrate DC pressures (P) as a function of time (t), said pressures being separated by means of AC/DC signal separators 13 and 14 from the signals received from pressure-sensing means 9 and 12. A curve A indicates a pressure signal detected by pressure-sensing means 9 and a curve B indicates a pressure signal detected by pressure-sensing means 12. FIG. 4a illustrates a signal obtained by an apparatus of FIG. 1, relating to the use of a cuff for newborn babies and a flow-restricting element 24. As shown in this figure, the pressure (curve A) rises in tube 3 upstream of a flow-restricting element very rapidly as the pumping is commenced. Instead, the pressure (curve B) on the other side of a flow-restricting element rises slowly, since the pressure is not at once capable of bursting through said element. Thus, the pressures detected by the different pressure-sensing means differ substantially from each other. The pressure increase indicated by curve A in FIG. 4a is only allowed to continue up to a certain limit for safety reasons. When this limit is reached, a pressure restricting element 8, preferably a relief valve, opens automatically to prevent the pressure increase above this limit. As the pressures are equalized on either side of said pressure restricting element, the measurement of blood pressure can be effected.

Often, when using a flow-restricting element in the identification of smaller cuffs, it is preferred that the identification of a cuff be attempted even twice at the early stages of pumping. In that case, a pump 2 can be stopped after a first identification and the pressures can be allowed to equalize on either side of flow-restricting element 24. This is followed by pumping a pressure in the system and using both pressure-sensing means 9 and 12 to monitor the pressure until a sufficient pressure difference is detected, whereby the pumping is stopped and the pressures allowed to equalize. If both identifications have indicated that a smaller cuff is being being used, the cuff can be normally inflated for measuring the blood pressure of newborn babies. An advantage offered by several identifications when identifying a smaller cuff is the possibility of more reliably detecting possible errors, such as tube blockings etc., occurred in identification.

On the other hand, FIG. 4b illustrates a signal obtained by an apparatus of FIG. 2. Hence, this relates to a cuff for adults. As shown in the figure, the pressure (curve A and B) detected by pressure-sensing means 9 and 12 rises almost simultaneously on either side of a cuff. Since there are no major pressure differences in the pressures measured at various locations, said control element 15 concludes that an adult cuff is coupled on.

Thus, a cuff can be pumped to a pressure sufficient for sphygmomanometry without interrupting the pumping in between for identification purposes.

FIGS. 4a and 4b indicate further that the identification of a cuff type can also be effected during the deflation of a cuff pressure, since a sufficient pressure difference occurs also at this stage in the identification of a cuff for infants by virtue of a flow-restricting element. When identifying an adult cuff, such pressure difference hardly ever occurs.

In order to avoid errors in the identification of a cuff, it would be beneficial if the pressure differences detected by pressure-sensing means 9 and 12 were of sufficient order, e.g. 40 mmHg. The control element would recognize a cuff type as fit for adults if the pressure difference during the course of pumping did not reach this limit value and, accordingly, if this limit value were exceeded, the control element would recognize a cuff as fit for infants.

The control element 15 conforms the functions of the device to those of a small cuff if it detects that the pressures measured at various points differ sufficiently from each other. In case of a cuff 6 for infants, the pressure to be pumped in the cuff remains lower than that in the case of an adult cuff 19. It is beneficial to take a cuff type into consideration also when deflating the pressure out of a cuff.

In order not to attach a larger cuff by mistake to a spacer element 4 provided with a flow-restricting element 24, it is preferable to equip said spacer element with such a coupling which is only compatible with small cuffs. It would also be preferable if a smaller cuff could not be attached to tubes 3 and 11 without a spacer element.

A flow-restricting element applicable in a cuff-type dentification method of the invention divides a pneumatic system into two sections. Hence, the rapid pressure fluctuations occurring between a flow-restricting element and a pressure-control system are visible in a more subdued form in the section of a system between flow-restricting element 24 and second pressure-sensing means 12. Thus, in the actual sphygmomanometry, it is preferable to employ just this pressure-sensing means 12.

Thus, a flow-restricting element 24 prevents the development of faults as the cuff pressure is continuously lowered by opening and closing a valve. The same way, a flow-restricting element prevents the passage of disturbances or faults to a cuff and to a pressure-sensing means during the course of pumping in a gas or a fluid. Another advantage offered by a flow-restricting element is that it also intensifies or strengthens the pressure pulses to be detected by pressure-sensing means 12 and applied to a cuff, and this is highly important when measuring the blood pressure on infants due to the small volume of a cuff intended for infants. Thus, the flow-restricting element serves as a reducer of the dead space in a long tube.

The invention is by no means limited to the above embodiments but various details of the invention can be modified within the scope of the claims.

Two pressure-sensing means are not absolutely necessary if there is some other way of measuring pressure at two different locations. One possibility would be pass tubes from either side of a flow-restricting element to a valve which, e.g. in an alternating fashion, would switch on a communication from either one of the tubes to one and the same pressure-sensing means.

If there is only two cuff types to be identified, it is sufficient to monitor the pressure development at two different points in a flow chamber included in one of the cuff types. The identification from two different points occurs most preferably whenever the flow manifold is provided with a flow-restricting element.

Neither is the invention limited to any given flow-restricting element. However, the most important feature is the ability to restrict a flow between those two different points that the pressure is being measured at.

We claim:

1. A method for identifying which cuff of at least a pair of cuffs is connected to a fluid conduit of a sphygmomanometer, the sphygmomanometer pressurizing the cuff or an associated enclosed volume in fluid communication with the cuff, one of the cuffs including means for altering pressure changes applied to the cuff or associated volume, said method comprising the steps of:
   applying a change in pressure to at least one of the cuff and the volume;
   sensing the pressure magnitude variations with respect to time occurring upstream of the cuff resulting from the change in pressure;
   sensing the pressure magnitude variations with respect to time occurring downstream of the cuff resulting from the change in pressure;
   comparing the pressure magnitude variations sensed upstream and downstream of the cuff, the presence or absence of the means for altering pressure changes in the cuff connected to the sphygmomanometer altering the sensed pressure magnitude variations; and
   determining from the comparison which cuff is connected to the sphygmomanometer.

2. The method according to claim 1 wherein the one of the cuffs is further defined as including a flow restricting means for altering pressure changes, and wherein the determination step is further defined as determining from the comparison of pressure magnitude variations whether the cuff having the flow restricting means is connected to the sphygmomanometer.

3. The method according to claim 1 wherein the determining step is further defined as determining from the comparison which cuff is connected to the sphygmomanometer as a result of pressure magnitude differences occurring in the sensed pressure magnitude variations that deviate from a predetermined pressure magnitude difference value.

4. The method according to claim 2 further defined as a method for determining whether a cuff intended for use with adult patients or a cuff intended for use with other than adult patients is connected to the sphygmomanometer and wherein the cuff intended for use with other than adult patients has the means for altering pressure changes.

5. The method according to claim 1 wherein the step of applying a pressure change is further defined as increasing the pressure.

6. The method according to claim 1 wherein the step of applying a pressure change is further defined as decreasing the pressure.

7. The method according to claim 1 wherein the step of applying a pressure change is further defined as applying a pressure change as part of a procedure for sphygmomanometrically measuring the blood pressure of a patient to whom the cuff is applied.

8. The method according to claim 7 wherein the claimed method is further defined as being carried out each time the blood pressure of the patient is sphygmomanometrically measured.

9. A method for identifying which cuff of at least a pair of cuffs is connected in a fluid circuit of a sphygmomanometer, the sphygmomanometer applying pressure to the cuff or an associated enclosed volume in fluid communication with the cuff, one of the cuffs including means for altering changes in pressure applied to the cuff or associated volume, said pressure change altering means having a first end to which pressure from the sphygmomanometer is applied and a second end at which the altered pressure change appears, said method comprising the steps of:
   applying a change in pressure to at least one of the cuff and the volume;
   sensing pressure magnitude variations with respect to time occurring as a result of the applied pressure change at a first point in the fluid circuit that would be in fluid communication with said first end of said pressure change altering means if said means is present;
   sensing pressure magnitude variations with respect to time occurring as a result of the applied pressure change at a second point in the fluid circuit that would be in fluid communication with said second end of said pressure change altering means if said means is present;
   comparing the pressure magnitude variations sensed at said first and second points; and
   determining from the comparison whether the pressure change altering means is present or absent and which cuff is connected to the sphygmomanometer.

10. The method according to claim 9 wherein said pressure change altering means is connected in series with said one of the cuffs or its associated volume in said fluid circuit and wherein the steps of sensing the pressure magnitude variations are further defined as sensing the pressure magnitude variations with respect to time occurring at a first point upstream of said pressure change altering means and as sensing the pressure magnitude variations with respect to time occurring at a second point downstream of the pressure change altering means.

11. The method according to claim 9 wherein the one of the cuffs is further defined as including a flow restricting means for altering pressure changes, and wherein the determination step is further defined as determining from the comparison of pressure magnitude variations whether the cuff having the flow restricting means is connected to the sphygmomanometer.

12. The method according to claim 10 wherein the one of the cuffs is further defined as including a flow restricting means for altering pressure changes, and wherein the determination step is further defined as determining from the comparison of pressure magnitude variations whether the cuff having the flow restricting means is connected to the sphygmomanometer.

13. The method according to claim 9 wherein the determining step is further defined as determining from the comparison which cuff is connected to the sphygmomanometer as a result of pressure magnitude differences occurring in the sensed pressure magnitude variations that deviate from a predetermined pressure magnitude difference value.

14. The method according to claim 9 further defined as a method for determining whether a cuff intended for use with adult patients or a cuff intended for use with other than adult patients is connected to the sphygmomanometer and wherein the cuff intended for use with other than adult patients has the pressure altering means.

15. The method according to claim 9 wherein the step of applying a pressure change is further defined as applying an increase in pressure.

16. The method according to claim 9 wherein the step of applying a pressure change is further defined as applying a decrease in pressure.

17. The method according to claim 9 wherein the step of applying a pressure change is further defined as applying a pressure change as part of a procedure for sphygmomanometrically measuring the blood pressure of a patient to whom the cuff is applied.

18. The method according to claim 17 wherein the claimed method is further defined as being carried out each time the blood pressure of the patient is sphygmomanometrically measured.

* * * * *